United States Patent [19]
Goffi

[11] Patent Number: 4,880,678
[45] Date of Patent: Nov. 14, 1989

[54] DRY TRANSFER SHEET

[75] Inventor: Italo Goffi, Alba, Italy

[73] Assignee: Miroglio Tessile S.p.A., Cuneo, Italy

[21] Appl. No.: 208,432

[22] Filed: Jun. 20, 1988

[30] Foreign Application Priority Data

Jun. 19, 1987 [IT] Italy .............................. 53445/87[U]

[51] Int. Cl.[4] .............................................. A61F 13/02
[52] U.S. Cl. ...................................... 428/40; 428/195; 428/212; 428/352; 428/484; 428/488.1; 428/488.4; 428/913; 428/914; 428/413; 428/414; 428/518; 428/520; 428/522
[58] Field of Search ................. 428/40, 212, 352, 195, 428/484, 488.1, 488.4, 913, 914, 413, 414, 518, 520, 522; 427/148

[56] References Cited

U.S. PATENT DOCUMENTS

| | | | |
|---|---|---|---|
| 4,670,307 | 6/1987 | Onish et al. | 428/212 |
| 4,681,796 | 7/1987 | Maehashi et al. | 428/212 |
| 4,707,395 | 11/1987 | Ueyama et al. | 428/212 |
| 4,708,903 | 11/1987 | Tanaka et al. | 428/212 |

*Primary Examiner*—Ellis P. Robinson
*Assistant Examiner*—P. J. Ryan
*Attorney, Agent, or Firm*—Sughrue, Mion, Zinn, Macpeak & Seas

[57] ABSTRACT

A dry transfer sheet comprises a colored film adhering to a backing sheet with the interposition of a layer or release varnish. The colored film includes a pigment, an acrylic polymer, a cycloaliphatic epoxy resin, a vinyl copolymer, a polyethylene wax, and the layer of release varnish includes an acrylic polymer, a vinyl copolymer and a polypropylene wax.

2 Claims, 1 Drawing Sheet

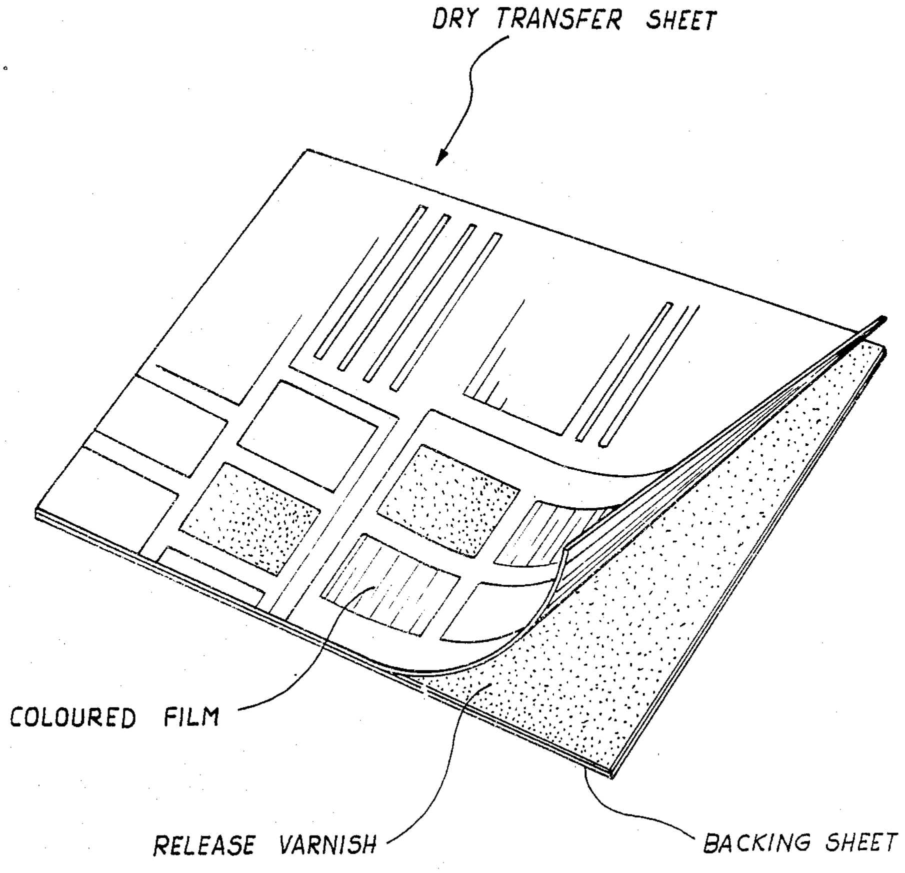
DRY TRANSFER SHEET
COLOURED FILM
RELEASE VARNISH
BACKING SHEET

DRY TRANSFER SHEET

The present invention relates to a dry transfer sheet comprising a coloured film adhering to a backing sheet with the interposition of a layer of release varnish.

The object of the present invention is to provide a sheet of the above type which enables the application of transfers on to rigid substrates of various types, preferably wood or metal, without the need for any preliminary treatment of the support. According to the invention, this object is achieved by virtue of the fact that the coloured film includes from 30 to 40% of pigment, from 15 to 35% of acrylic polymer, from 1 to 4% of cycloaliphatic epoxy resin, from 15 to 35% of vinyl copolymer, from 1 to 4% of polyethylene wax, and by virtue of the fact that the layer of release varish includes from 40 to 80% of acrylic polymer, from 15 to 40% of vinyl copolymer and from 5 to 20% of polypropylene wax.

By virtue of the above compositions, expressed as percentage by weight, the application of the transfer can be effected in a press or a calender at temperatures no greater than 130° for times of approximately 3–5 seconds, avoiding the problems of excessive heating of the rigid support, which exist, for example, in the printing of rigid supports by means of the so-called "transfer" technique.

The dry transfer sheet according to the invention is particularly suitable for printing on to panels of wood. In fact the reduced heating of the panel which is possible with the transfer according to the invention avoids any deformation of the panel itself and the transfer can, moreover, be applied to untreated wood, to which a transparent lacquer varnish can subsequetly be applied further to protect the transfer and considerably increase its life.

The coloured film preferably includes from 0.5 to 3% of dibutylethane carboxylate-based stabiliser and the dry transfer sheet is preferably printed on to the rigid substrate at a temperature of between 100 and 130° C. The application both of the release varnish and of the coloured film to the backing sheet, which is normally a krafty-type paper or a polypropylene film, is wholly conventional, with the useof suitable solvents. The solvent most commonly used for the application of the release varnish to the paper backing sheet is a mixture of water with isopropyl alcohol and ethyl alcohol. The solvent normally used for the voloured film is constituted by a mixture of ethyl acetate, ethylene glycol acetate and methyl ethylketone.

Further characteristics and advantages of the dry transfer sheet according to the present invention will become clear from the following examples which in no way limit the scope of the invention.

EXAMPLE 1

A release varnish of the following composition was used:

| | |
|---|---|
| acrylic polymer | 30% |
| vinyl copolymer | 13.5% |
| polypropylene wax | 5% |
| coalescent agent | 3% |
| water | 22% |
| isopropyl alcohol | 10% |
| ethyl alcohol | 11.5% |
| antistatic agent | 5% |

After the above release varnish had been applied to a paper backing, a coloured film was applied thereto, whose composition at the time of application was as follows:

| | |
|---|---|
| red pigment | 17% |
| acrylic polymer | 10% |
| ethyl acetate | 18.9% |
| ethylene glycol acetate | 4.6% |
| methyl ethyl ketone | 38% |
| cycloaliphatic epoxy resin | 1% |
| vinyl copolymer | 9% |
| polyethylene wax | 1% |
| dibutylethane carboxylate-based stabiliser | 0.5% |

After application of the release varnish and the coloured film to the paper backing and drying thereof, the competitions of the layer of the release varnish and that of the coloured film are as follows:

| release layer | |
|---|---|
| acrylic polymer | 62% |
| vinyl copolymer | 27,7% |
| polypropylene wax | 10,3% |
| colored film | |
| red pigment | 44,1% |
| acrylic polymer | 26,0% |
| cycloaliphatic epoxy resin | 2,6% |
| vinyl copolymer | 23,4% |
| polyethylene wax | 2,6% |
| dibutylethane carboxylate-based stabiliser | 1,3% |

After drying the sheet was arranged on a panel of veneered wood and the coloured film was released from the paper backing by compressin of the transfer thus obtained on to the panel of wood in a press at a temperature of approximately 115° for a time of from 3 to 5 seconds. Under these conditions perfect adhesion of the transfer to the panel of wood was obtained and it was subsequently treated with lacquer.

EXAMPLE 2

Release varnish having the same composition as in Example 1 was used.

The composition of the coloured film at the time of application was as follows:

| | |
|---|---|
| blue pigment | 18% |
| acrylic polymer | 10.5% |
| ethyl acetate | 16.25% |
| ethylene glycol acetate | 4.5% |
| methyl ethyl ketone | 39.5% |
| cycloaliphatic epoxy resin | 1% |
| vinyl copolymer | 8.75% |
| polyethylene wax | 1% |
| dibutylethane carboxylate-based stabiliser | 0.5% |

The conditions under which the transfer sheet thus obtained were applied were the same as in Example 1. The composition of the dried coloured film is as follows:

| | |
|---|---|
| blue pigment | 45.3% |
| acrylic polymer | 26.4% |
| vinyl copolymer | 22.1% |
| polyethylene wax | 2.5% |
| dibutylethane carboxylate- | 1.2% |

-continued

| |
|---|
| based stabiliser |

Good results have been also obtained using coloured film including (in the dried condition) from 40 to 50% by weight of pigment, from 20 to 30% of acrylic polymer, from 1 to 3% of cycloaliphatic epoxy resin, from 20 to 30% of vinyl copolymer and from 2 to 3% of polyethylene wax. With a coloured film having the above concentrations, the layer of release varnish preferably includes (in the dried condition) from 50 to 70% of acrylic polymer, from 20 to 35% of vinyl copolymer and from 5 to 15% of polypropylene wax.

I claim:

1. A dry transfer sheet comprising a coloured film adhering to a backing sheet with the interposition of a layer of release varnish, characterized in that the coloured film includes from 30 to 50% by weight after curing of pigment, from 15 to 35% of acrylic polymer, from 1 to 4% of cycloaliphatic epoxy resin, from 15 to 35% of vinyl copolymer, from 1 to 4% of polyethylene wax, and in that the layer of release varnish includes from 40 to 80% of the acrylic polymer, from 15 to 40% of vinyl copolymer and from 5 to 20% of polypropylene wax.

2. A sheet according to claim 1, characterized in that the coloured film also includes from 0.5 to 3% of dibutylethane carboxylate-based stabiliser.

* * * * *